United States Patent [19]
Fontenot et al.

[11] Patent Number: 5,910,816
[45] Date of Patent: Jun. 8, 1999

[54] IMAGING SYSTEM WITH INDEPENDENT PROCESSING OF VISIBLE AN INFRARED LIGHT ENERGY

[75] Inventors: Mark G. Fontenot, Lafayette, La.; Richard Feinberg, Bellingham, Wash.; Howard Katz, Potomac, Md.

[73] Assignee: Stryker Corporation, Santa Clara, Calif.

[21] Appl. No.: 08/663,015

[22] Filed: Jun. 7, 1996

Related U.S. Application Data

[63] Continuation-in-part of application No. 08/472,785, Jun. 7, 1995, abandoned.

[51] Int. Cl.⁶ .................................................. H04N 07/18
[52] U.S. Cl. ............................... 348/65; 348/68; 348/70; 348/162; 348/164; 348/77; 600/109
[58] Field of Search ............................. 348/65, 67, 68, 348/69, 70, 72, 77, 162, 164, 166, 168, 66; 600/109, 921; 128/664, 665, 666

[56] References Cited

U.S. PATENT DOCUMENTS

| | | | |
|---|---|---|---|
| 3,886,933 | 6/1975 | Mori et al. ................................. | 128/7 |
| 4,248,214 | 2/1981 | Hannah et al. . | |
| 4,303,298 | 12/1981 | Yamashita ............................... | 350/311 |
| 4,751,571 | 6/1988 | Lillquist .................................. | 348/164 |
| 4,806,761 | 2/1989 | Carson et al. ........................... | 348/164 |
| 4,817,622 | 4/1989 | Pennypacker et al. .................. | 348/77 |
| 4,898,175 | 2/1990 | Noguchi .................................. | 128/634 |
| 4,967,276 | 10/1990 | Murakami et al. ...................... | 348/164 |
| 5,168,873 | 12/1992 | Seifert et al. . | |
| 5,187,572 | 2/1993 | Nakamura ................................ | 348/72 |
| 5,293,872 | 3/1994 | Alfano et al. ............................ | 128/664 |
| 5,423,321 | 6/1995 | Fontenot .................................. | 128/664 |
| 5,515,449 | 5/1996 | Tsuruoka et al. ........................ | 382/128 |
| 5,517,997 | 5/1996 | Fontenot .................................. | 128/664 |
| 5,540,677 | 7/1996 | Sinofsky .................................... | 606/8 |
| 5,603,328 | 2/1997 | Zucker et al. ............................ | 128/664 |
| 5,606,969 | 3/1997 | Butler et al. .......................... | 128/653.1 |
| 5,667,474 | 9/1997 | Nishimura .............................. | 600/109 |

FOREIGN PATENT DOCUMENTS

| | | |
|---|---|---|
| 0512965 | 11/1996 | European Pat. Off. .......... A61B 5/00 |
| 2102127 | 2/1983 | United Kingdom . |
| WO 9005426 | 5/1990 | WIPO ........................... H04N 5/238 |
| WO 91/11956 | 8/1991 | WIPO . |
| WO 9511624 | 5/1995 | WIPO . |

OTHER PUBLICATIONS

"Laparoscopic Transillumination for the Location of Anterior Abdominal Wall Blood Vessels", Elisabeth H. Quint, M.D. et al, Journal of Laparoendoscopic Surgery, vol. 6, No. 3, 1996; pp. 167–169.

"An Investigation of an Infrared Ray Electronic Endoscope with a Laser Diode Light Source", H. Kohso et al, Endoscopy 22 (1990) pp. 217–220.

"Light Reflection Rheography: A Saimple Noninvasive Screening Test for Deep Vein Thrombosis", Subodh Arora et al, Journal of Vascular Surgery, Nov. 1993, pp. 767–772.

"Indocyanine Green Dye Flourescence and Infrared Absorption Choroidal Angiography Performed Simultaneously with Fluorescein Angiography", R.W. Flower and B.F. Hochheimer, The Johns Hopkins Medical Journal, vol. 138 No. 2, Feb. 1976, pp. 33–37.

*Primary Examiner*—Tommy P. Chin
*Attorney, Agent, or Firm*—Howard L. Rose

[57] ABSTRACT

In order to protect body members adjacent an invasive procedure on a body, the member to be protected is illuminated preferably with infrared light energy and the entire site of the invasive procedure is viewed through an optical system that conducts both infrared and visible light energy to one or more video cameras. Various structures may be employed to separate the visible and infrared light energies so that the signals representing such light energies may be processed separately and differently if desired and then recombined for display or separately displayed on a video color monitor.

36 Claims, 7 Drawing Sheets

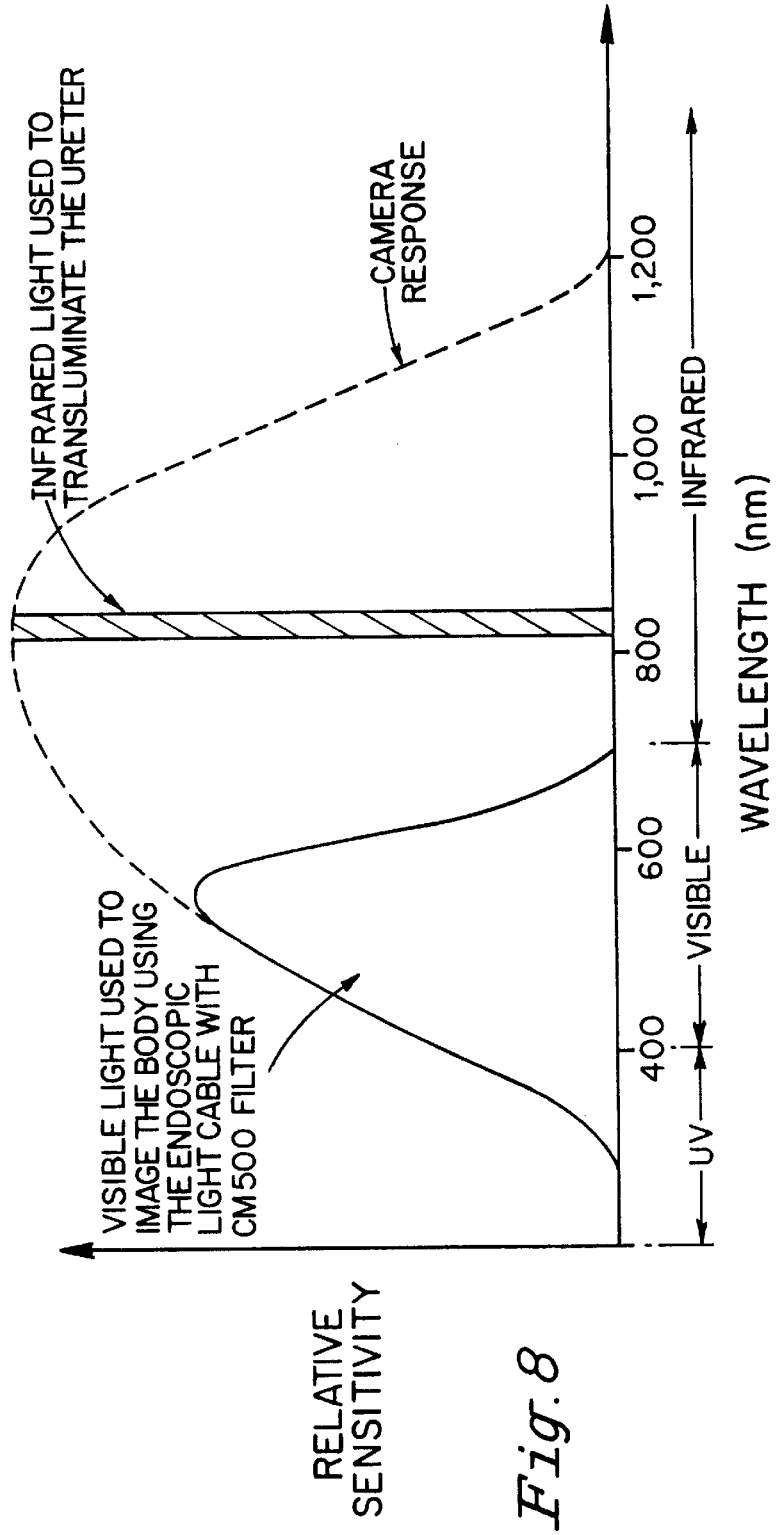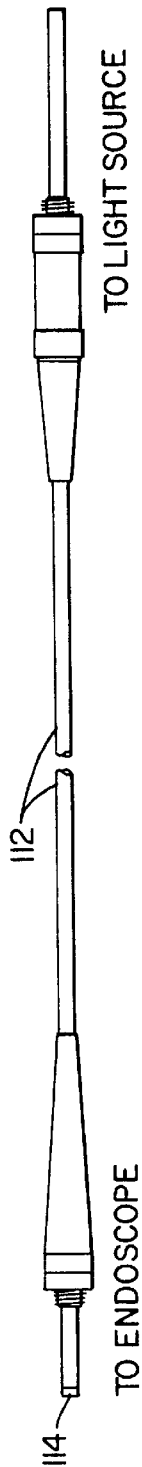

IMAGING SYSTEM WITH INDEPENDENT PROCESSING OF VISIBLE AN INFRARED LIGHT ENERGY

RELATED APPLICATIONS

This application is a continuation-in-part of U.S. patent application Ser. No. 08/472,785 filed Jun. 7, 1995 (now abandoned). It is related to U.S. patent application Ser. No. 08/355,164 filed Dec. 8, 1994 (still pending), and entitled "Transillumination of Body Members for Protection During Body Invasive Procedures", a continuation-in-part of U.S. patent application Ser. No. 08/305,296 filed Sep. 15, 1994 (now U.S. Pat. No. 5,517,997), of the same title, U.S. patent application Ser. No. 08/190,516 filed Feb. 2, 1994 (now U.S. Pat. No. 5,423,321), a continuation-in-part of U.S. patent application Ser. No. 08/016,565 filed Feb. 11, 1993 (now abandoned), both entitled "Detection of Anatomic Passages Using Infrared Emitting Catheter".

FIELD OF THE INVENTION

The present invention relates to methods and apparatus for imaging the site of an operation as well as various body parts in the region of an operation and more particularly to simultaneous or alternate display of the site of the operation as well as organs, passages, etc., in the region of the operation to avoid inadvertent damage to such organs, passages, vessels and the like.

BACKGROUND OF THE INVENTION

In prior applications of one of the present inventors, there are disclosed various methods and apparatus for illuminating, primarily, though not necessarily, with infrared, various body parts in the region of a body invasive procedure which body parts are to be protected against inadvertent cutting or other damage or trauma. Infrared light energy is preferred since such energy penetrates surrounding tissue to a significantly greater extent than visible light. In this regard see application Ser. No. 08/355,164 filed Dec. 8, 1994, pages 27 and 28.

In one such exemplary method of the use of the infrared light energy in surgery, a catheter is inserted into the ureter of a patient and a light guide is inserted into the catheter. The light guide is modified such that a predetermined length of the distal end of the guide will, when the proximate end is connected to an infrared light source, emit infrared light energy generally transverse to the length of the guide. Various means may be used to detect the infrared light energy and thus locate the body member to be protected.

The various means for detecting the infrared light energy may include a video camera sensitive to such energy, means for display of an image thus produced on a monitor along with images of the site of the operation, a detector that provides an audible or visual indication of the location of the body member to be protected or a combination of both approaches.

In the systems as presented in the prior applications the visual and infrared images are processed through the same signal channels, it was not possible with the equipment disclosed therein to independently manipulate the signals to selectively enhance one set of signals relative to the other or to apply various digital techniques to both signals to enhance viewing of the site of the procedure. Further since infrared and visual light do not normally focus at the same distance from an imaging lens one of the images may be slightly blurred relative the other.

An additional problem that has developed is in the use of an endoscopic light source. The source introduces infrared light into the region of the surgery or of investigation. Such additional infrared light reduces the gain of the system to infrared light. Further the removal of the IR filter from the laparoscopic camera reduces certain color compensation provided by such filter and, for instance, causes dried blood to look almost black instead of dark red.

OBJECTS OF THE INVENTION

It is an object of the present invention to provide an infrared and visible light energy viewing system permitting independent processing and display on a color monitor of signals related to the different sources of light energy.

It is another object of the present invention to provide a system for protecting against damage to a body member adjacent a surgical site or other body invasive procedure by illuminating the member to be protected with infrared light energy, illuminating the site with visible light energy and displaying concurrently or alternatively after independent processing of the light signals the surgical site together with the view provided by the infrared light energy all on a color monitor.

It is yet another object of the present invention to display concurrently on a color monitor naturally generated color signals of a surgical site and falsely generated color signals of certain elements in the region of the surgical site.

It is still another object of the present invention to view a scene that radiates both color signals and infrared signals, to process the signals independently and display them on a color monitor with or without manipulation of the color signals and with or without false color added to the infrared light signals while permitting control of how the signals are to be displayed individually or concurrently.

Yet another object of the present invention is to collect both color signals and infrared signals from a site and to process the signals for subsequent display in separate channels or in a single channel.

Another object of the present invention is to add to an endoscope an infrared blocking and color compensating filter whereby no IR light is introduced into a surgical site by the endoscopic light source and color produced in the viewing region is compensated to provide a realistic image of the site.

Yet another object of the present invention is to remove from a laparoscopic camera employed in viewing a surgical site or site of a body invasion procedure, an IR blocking and color enhancing filter and adding the filter to an endoscopic light source path whereby to increase the camera's response to infrared light energy from a source of light other than the endoscopic source.

BRIEF DESCRIPTION OF THE PRESENT INVENTION

In accordance with one embodiment of the present invention, independent visual light and infrared light paths are provided whereby processing of the signals from an imaging lens may be accomplished independently of one another. Specifically, light from an imaging lens or endoscopic coupling lens is directed to a beam splitter prism having a dichroic filter oriented at 45° to the direction of the propagation axis of the light (optical axis). The visible light proceeds directly through the prism to a standard color CCD camera chip mounted at the exit region of light from the prism along the optical axis. An infrared blocking filter is normally placed in front of the CCD of the standard video color camera and in this situation it is removed from the camera and placed in the visual light path to eliminate any infrared light that may have passed through the dichroic filter. The signal from the visual light CCD may be processed conventionally or various enhancement techniques such as edge enhancement may be employed.

The infrared light energy is reflected from the dichroic filter at right angles to the optical path and directly to an infrared sensitive monochrome CCD camera chip. This chip is also mounted on an edge of the prism without or with a visible light blocking filter so as to eliminate any visual light that may have been reflected by the dichroic filter. Appropriate adjustment may be independently made in the length of the paths of the two light spectra through the prism to correct for the different focal lengths of the two light spectra.

The signal produced by the now infrared light sensitive CCD may be processed in a number of ways: gain enhancement, digital edge detection, addition of pseudocolor, etc. Further by adjusting the controls manually or electronically it is possible to display one or the other light image, alternate the displays or display both images at once. The ability to independently control gain of the images permits enhancement of one relative to the other when displayed concurrently or to provide equal intensity of display.

In an alternative embodiment of the present invention there is provided a method and system that does permit in a single channel independent displays and processing of visual and infrared light energy signals. In this latter embodiment an infrared blocking filter and a visual light blocking filter are arranged on a slide, rotatable disk or the like (hereinafter "slide") that by moving the slide inserts one or the other of the filters in the light path to an infrared sensitive color video camera. The original processing of the individual signals may be as in the preferred embodiment by switching various processing circuits in and out depending upon the position of the slide. The slide may also compensate for path length and the camera must be able to sense infrared light energy as well as visible light energy. Simultaneous display of light and infrared images is not directly achievable without storage in a system employing such a system but by employing for instance a rotating disk synchronized with the electronics of the system a display of great clarity of both images is possible. If storage of signals is employed, the signals of both images may be displayed at the same time, combined and displayed as a single set of signals or displayed separately.

In a still further system, a rotating disk has red, green and blue transmitting filters as well as an infrared transmitting filter all arranged in a circular path along the disk. The camera is a monochrome video camera and signal processing circuits synchronized with the electronics of the system produce the required color mix to reproduce the colors in the field of view. When the IR filter is in front of the camera, any desired visible color, such as purple or a very bright green, may be electronically substituted so that the body member to be protected shows up differently from the other areas of the surgical site and body members in the area. The infrared filter has compensating optics to correct for the different IR focal length of the common imaging optics.

It should be noted that the rotating wheel embodiment has advantages over the split prism approach in that there is no image inversion, it provides full motion video, has no registration errors and has a cost advantage as a result of the availability of off-the-shelf hardware.

Instead of the use of a rotating disk a liquid crystal shutter may be employed such as a Varispec RGB filter. The advantages of such are obvious because length of time of display of a single color is readily controlled. For instance, in a given situation the surgeon may find that a green only and IR display with false color provides him with the detail he desires. In this latter system (and in the rotating disk system if, for instance, a servomotor is employed) the surgeon has complete (and uncomplicated) control over the display. He can readily have a red false color display of the IR signal and thus have a red-green display of the different elements in the view. As indicated immediately above, the same effect is achievable with a rotating disk by moving only between a fixed color and IR segments using servo control. A bi-directional stepper motor may also be employed but does not provide quite the same flexibility as a servo control. It is also of interest that the liquid crystal filter can be used with the slide discussed above and with control of the crystal, a very simple but highly flexible system can be provided. In such a structure red, green and blue liquid crystal filters may be aligned in series in the optical path with each filter selectively energized by applying a voltage thereacross. Such a filter is available from Cambridge Research and Instrumentation of Cambridge, Mass. under the name "Varispec".

As indicated above the standard endoscopic camera has an IR filter over the silicon CCD; this filter also supplying color compensation to the light received from the site of the procedure. According to the present invention this filter is removed from the camera and placed in the path of the light from the endoscopic light source. This procedure produces several results in numerous benefits. It results in rendering the camera sensitive to infrared light while preventing the endoscope from introducing infrared light energy into the site of the procedure which would reduce the response of the camera to the infrared light from the IR source. Further the filter removed from the camera has color compensation included in it so that the color display on the monitor is more realistic and approximates the color rendition previously produced by the filter when located in front of the CCD of the camera.

In accordance with the invention, the light cable from an endoscopic light source to an endoscope houses a filter that blocks infrared from the light source and adds a cyan color to the light. The Hoya CM500 light filter is cyan in color, blocks near infrared light and adds color to the light illuminating the surgical field. To the naked and unaided eye, the light exiting the light cable appears cyan in color. However, this cyan filtered light that illuminates the surgical field corrects or compensates for reflected light from organs and instruments during an endoscopic procedure that is captured by the laparoscopic camera. The net effect is an improvement in the color fidelity of the imaged field using the aforesaid camera.

The following must be accomplished in order for a camera to render an image of true color fidelity.

1. The CM500 infrared and color compensating filter must be removed from the camera and replaced with a filter that is transparent to visible and infrared light.
2. The CM500 compensating filter or other appropriate filter is placed between the endoscopic light source and the surgical field. Note, in the typical endoscopic camera, the CM500 filter is located between the surgical field and the CCD.
3. The light incident in the body cavity during endoscopic procedures using an endoscopic cable with the CM500 color compensating filter is free of infrared and is cyan colored.

4. Other color compensating filters can be used on other than xenon and metal halide light sources to correct for cameras that are set up for other light sources.

The above and other features, objects and advantages of the present invention, together with the best means contemplated by the inventor thereof for carrying out the invention will become more apparent from reading the following description of various embodiments of the invention and perusing the associated drawings in which:

BRIEF DESCRIPTION OF THE DRAWINGS

FIG. 8 is a graph of the sensitivity of the laparoscopic camera(s) to visible and infrared light energy;

FIG. 9 is a view of the endoscope with a color correcting and infrared blocking filter attached thereto.

DETAILED DESCRIPTION OF THE PRESENT INVENTION

Figure 1:
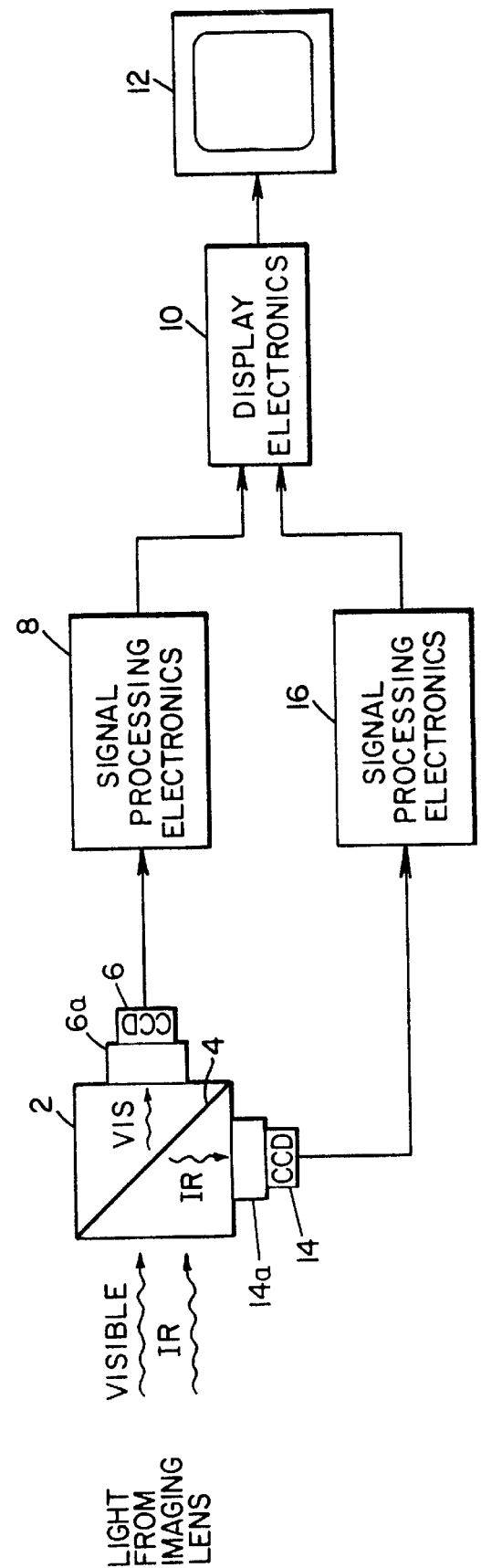
FIG. 1 of the accompanying drawings illustrates a beam splitter and following circuitry employed in practice of the present invention.

Referring specifically to FIG. 1 of the accompanying drawings there is illustrated an imaging system according to a first embodiment of the present invention. A beam splitter prism 2 has a dichroic filter 4 extending at approximately 45° from the upper left hand corner of the prism to the lower right hand corner. Light from an imaging lens enters the prism from the left as viewed in FIG. 1 and visual light proceeds directly through the filter along the optical axis of the light to the right edge of the prism. A charge coupled device (CCD) color camera chip 6 is secured to the right vertical surface (as viewed in FIG. 1) of the prism 2. The chip 6 is equipped with the standard infrared blocking filter (6a) so that any infrared light energy that does penetrate the dichroic filter is blocked at the CCD. The output signal from the chip is applied via signal processing electronics 8 and display electronics 10 to a color TV monitor 12 where the color images may be displayed.

Infrared light energy entering the prism 2 along the optical path is deflected, by the dichroic filter, in this instance 90°, so as to proceed at right angles to the optical path and impinge upon a second CCD 14 of a camera. The CCD 14 has had the conventional infrared light energy blocking filter omitted so that this camera is sensitive to such light energy. If convenient a visible light blocking filter 14a to eliminate visible light that may have been deflected by the filter 4 may be employed.

The infrared image is reversed relative to the visible light image. This problem can be corrected by the use of corrective lenses or by use of a prism employing an even number of reflections or by digitizing all signals and employing conventional digital techniques to reverse the infrared image. Such an approach requires an A/D converter and a store that can reverse the digits on interrogation such as disclosed in U.S. Pat. No. 3,756,231 to Faustini.

The CCD 14 is a monochrome sensitive chip with high IR sensitivity. The output signal from the chip 14 proceeds via signal processing electronics 16, and the display electronics 10 to the monitor 12.

The signals from the signal processing electronics 8 and 16 are combined in the display electronics 10 so that the display on the monitor 12 is a composite of the two signals. Normally as a result of chromatic aberration visible light and infrared light do not focus at the same distance from an imaging lens resulting in a partially blurred image of either the visible light or infrared light image. This problem is readily corrected in accordance with the present invention by making the prism rectangular so that one path is longer than the other to the extent necessary to correct focal length or by inserting a filter of the proper depth. Specifically, the path of the infrared light is made longer than that of the visible light.

The imaging lens may be an endoscopic imaging lens. Such a lens is also used in co-pending application Ser. No. 08/305,296 filed Sep. 15, 1994, the entire disclosure of which is incorporated herein by reference. Alternatively the lens may be that of the optical instrument illustrated in FIG. 4 of U.S. patent application Ser. No. 08/190,516 having a Notice of Allowance issued therein. The disclosure of such application is also incorporated herein by reference. Such lenses are available from Universe Kogaku or F Prime Optics and others. The designations of right, left, up and down refer to the objects illustrated in FIG. 1 and are not limiting since the location of the lens, prism, CCDs, etc. may readily be changed as long as the relative location of the elements to the optical axis remain the same.

Figure 2:
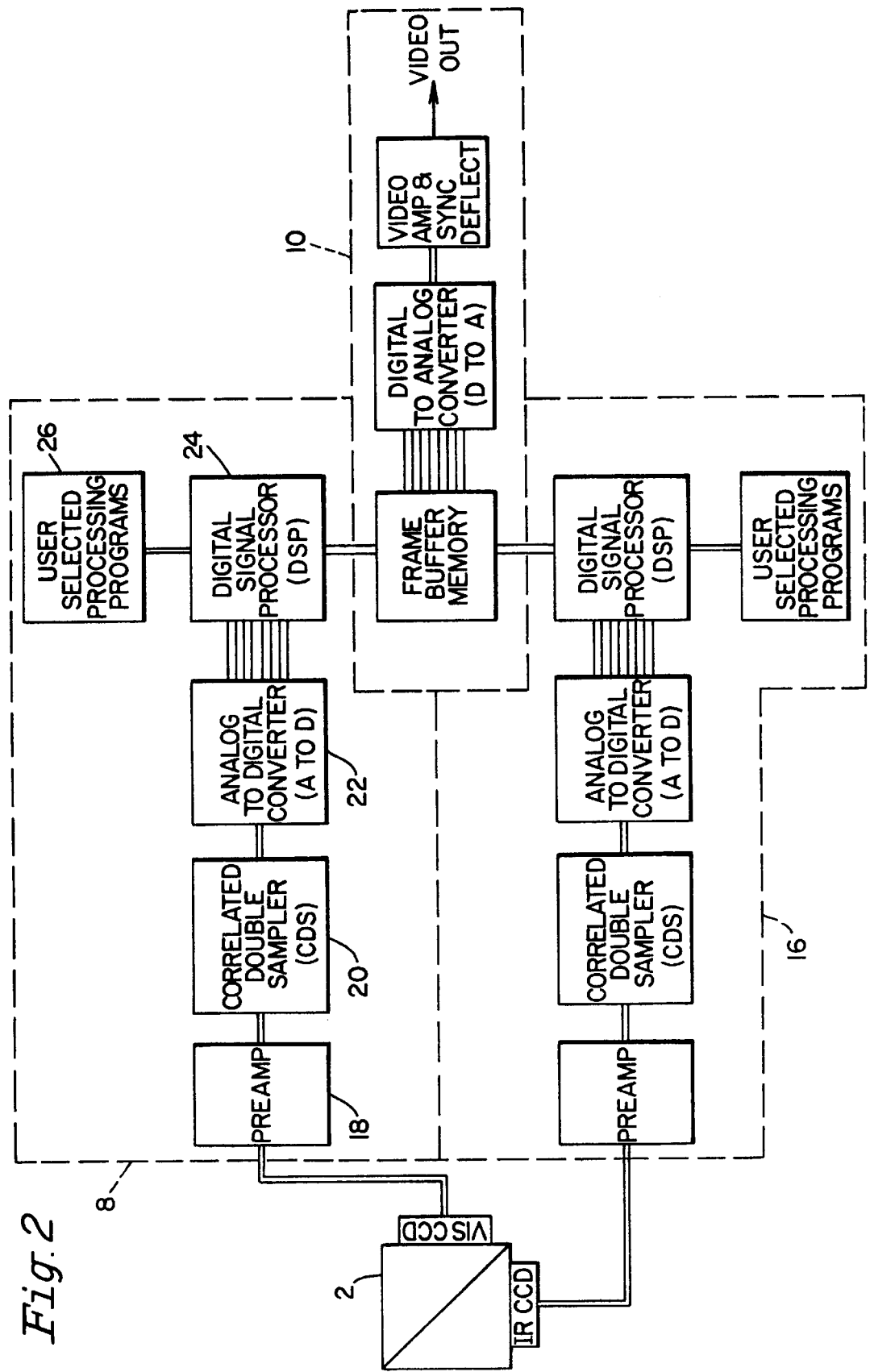
FIG. 2 is a block diagram of the signal processing circuits.

The circuitry of signal processing electronics are essentially standard signal processing circuits and a simplified system is illustrated in block diagram form in FIG. 2.

Referring to FIG. 2 of the accompanying drawings, the signal processing electronics includes and reference is made only to electronics 8 since the electronics of channels 8 and 16 may be identical, a preamp 18, correlated double sampler 20, and an analog-to-digital converter 22 for developing signals for processing by digital signal processor 24. The processing is controlled by user selected processing programs stored in memory 26. The program may include facility for edge enhancement, gain control, image coring, gamma control and the like. In the case of the element in processor 16 corresponding to element 26, color may be added to the infrared derived signal. It should be noted that the preamp 18 and other elements are employed in the other two embodiments of the invention.

The display electronics 10 includes all standard elements including, for instance, a frame buffer memory in which the signals of the two channels are stored frame by frame for synchronized transmission to a digital-to-analog converter where the signals are combined and fed to a video amplifier, sync generator and deflection control circuits and thence to a color monitor.

The elements employed are all standard items and the programs are relatively simple by today's standards.

Figure 3:
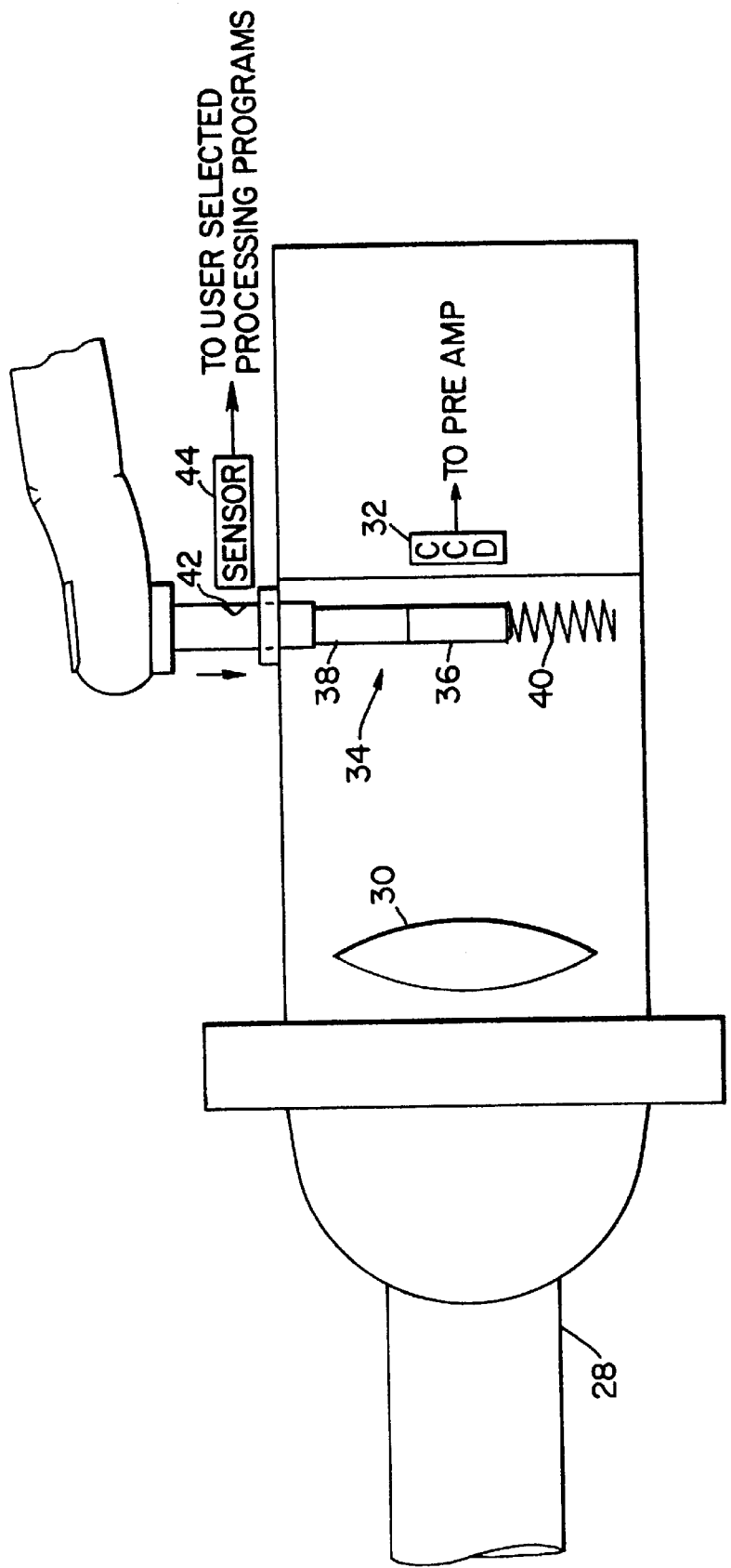
FIG. 3 illustrates a slide containing an infrared and a color filter to permit such signals to be processed in a single channel.

Referring now specifically to FIG. 3 of the accompanying drawings, there is illustrated a slide for use in a single channel system. An image carrying light guide 28 introduces light to a lens 30 that focuses light on a color video camera CCD 32 through a slide 34. The slide includes a color pass filter 36 and an IR pass filter 38 and is biased to an upward position as illustrated in FIG. 3 by a compression spring 40. The slide is configured to be operated by a surgeon or his/her assistant; the view can be changed by merely depressing the slide.

The CCD 32 has the IR blocking filter omitted so that it is sensitive to infrared light energy which when the filter 38 is depressed is passed to the CCD 32. The CCD 32 feeds its signals to a preamp, such as preamp 18 of FIG. 2, and thence through the circuits 8 or 16 of FIG. 2.

The slide 34 has a notch 42 or other detectable physical characteristic (magnet, mirror, etc.) that is detectable by a sensor 44. The sensor sends a signal to circuitry in communication with User Selected Processing Programs, such as stored in element 26 of FIG. 2 to select which program is to be in use, one for color—one for infrared. The two sets of signals may be displayed individually or stored and combined for concurrent display.

Figure 5:
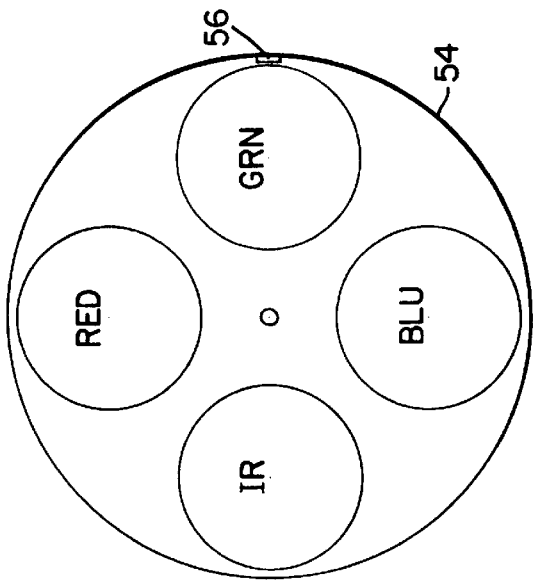
FIG. 5 illustrates a rotatable disk for use in the system of FIG. 3.
Figure 4:
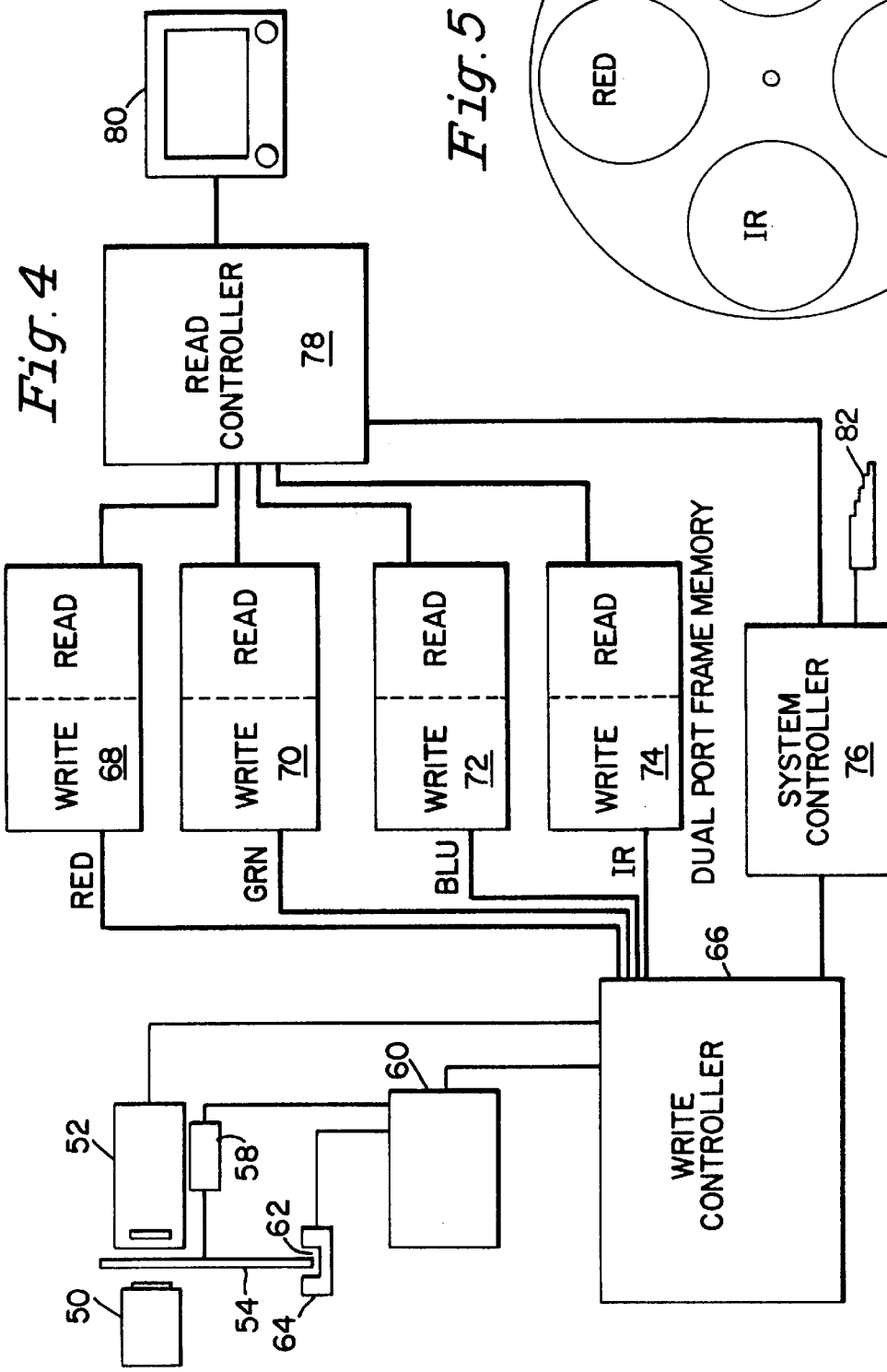
FIG. 4 illustrates a viewing system employing a single channel for independently processing color and infrared light energy signals.

Another single channel system is illustrated in FIGS. 4 and 5 of the accompanying drawings. This system employs only a monochrome CCD video camera with the IR blocking filter omitted and all color is provided by processing circuits.

Specifically, a lens 50 that receives light from a source via, for instance, an image carrying light guide, focuses light on a monochrome video CCD camera 52 through a circular filter wheel 54. The filter wheel 54, see FIG. 5, has red, green, blue and infrared pass filters disposed in a circular array about the filter wheel; the red, green and blue colors constituting the additive color primaries employed in video to process the complete visual spectrum. The filter wheel has an index notch 56 in its periphery for purposes described subsequently.

Returning to FIG. 4, the filter wheel 54 is rotated by a motor 58 under control of a motor controller 60. The periphery of the wheel 54 is rotated through a slot 62 in an index sensor 64 that produces a synchronizing signal for a specific position of the wheel. The signal from the index sensor is processed through the motor controller, where the angular position of the motor is controlled, and thence to a write controller 66.

The video camera 52 also supplies its output signals to the write controller which distributes signals to dual port frame memory circuits 68, 70 and 72 as determined by the position of the filter wheel. Thus, when a red filter is disposed between the lens 50 and the camera 52 the signal produced by camera 52 is gated to the circuit 68. Likewise green and blue signals are gated sequentially to circuits 70 and 72. In customary fashion these signals are converted to digital signals, applied to a lookup table and a signal of an intensity determined by the amplitude of, for instance, the incoming red signal, is made available to the "read" or output circuit of the write-read circuit 68. Similarly the signal produced when the IR filter disposed between the lens and camera is applied to IR write-read circuit 74 having its own lookup table.

The write controller 66 supplies indexed output control signals to system controller 76. The controller 76 outputs signals to a read controller 78. This element appropriately times the output of the system and also permits selection of which signals are to be displayed; color, infrared or both. Thus when a read circuit of say the red circuit is gated to the monitor, the read controller synchronizes this with impingement of the electron beam of monitor 80 on the red CRT phosphor.

As in FIG. 3, processing of the individual signals may take place as desired and may be accomplished in the read controller 78, the write-read circuits or both but most appropriately in the system controller 76. This controller may have input from a keyboard 82, RS232 input or rotary controls on a front panel. Control may be over color mix to highlight a particular element of the view, adding color particularly to the IR signal, or produce true color or an increase in color intensity and shading or providing "false" colors. Also the wheel 54 may be stopped so that a particular color element may be viewed for an extended time. There are no constraints on flexibility.

The same flexibility is available from the system of other designs, particularly the system of FIG. 1, the same degree of control being available from standard circuits employed in FIG. 3. In any event the system of FIG. 4 provides a single channel system using a monochrome camera with extreme flexibility and reasonable cost. The use of a single camera reduces cost and avoids the image inversion and registration problems of a prism based system. The physical components can be quite small particularly if they are to be used in an operating room or the like. The motor-disk structure may readily be smaller than illustrated in FIG. 4 so that the entire physical system produces no problems in an operating room.

The monochrome camera is available from ELMO TSE-270, the dual port frame memory may be a Fidelity 100 or Vision-EZ from Data Translation and others, the image software stored in the system controller 76 is available from NOESIS as Visilog or Image-Pro from Media Cybernetics and others. A circuit for processing the monochrome images to produce color is available from Cambridge Research & Instrumentation, Inc. under the name Varispec. The precision motor is available from Globe or Micro-Mo. The write controller via keyboard 82 or other input controls, if desired, may control all of the display functions; color, other processing such as edge enhancement, etc. as set forth above, all in conventional manner using conventional programs.

As indicated previously the color wheel may be replaced by a series of LCD color filters (red, green and blue) aligned in series and energized sequentially by well known techniques such as a rotary switch. The switch may be an electronic switch for rapid processing of signals and/or manually operated or keyboard controlled to permit the surgeon or an attendant to select a single color or even two of the three colors. The advantage of such a system is size and no mechanical inertia.

Figure 6:
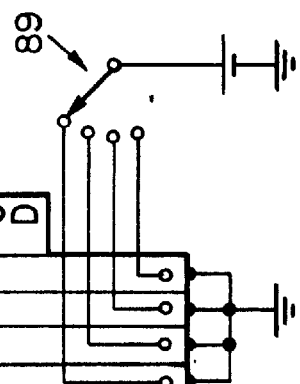
FIG. 6 illustrates a color separation system employing LCD filters.

The system is illustrated in FIG. 6 and is quite simple. It employs four LCD filters 81, 83, 85 and 87, filter 81 for IR and each of the others for a different color. A voltage control switch 89 illustrated as a mechanical switch for simplicity controls the ability of a filter to pass light of its color. A color or monochrome CCD 93 is also employed.

Each filter passes all light from IR through the visible spectrum except when energized. When energized it passes only the color for which it is designed. Thus when it is desired to pass IR only the filter 81 is energized and only infrared is passed through the system. Each of the other filters 83, 85 and 87 are energized in sequence so the red, green and blue are passed in sequence; the IR filters being in the sequence also. Thus a stationary color sequential system is provided with no moving parts.

The advantage of the apparatus of FIG. 6 is the elimination of the IR separation prism and the image reversal, path length and mechanical problems with some of the other embodiments.

Figure 7:
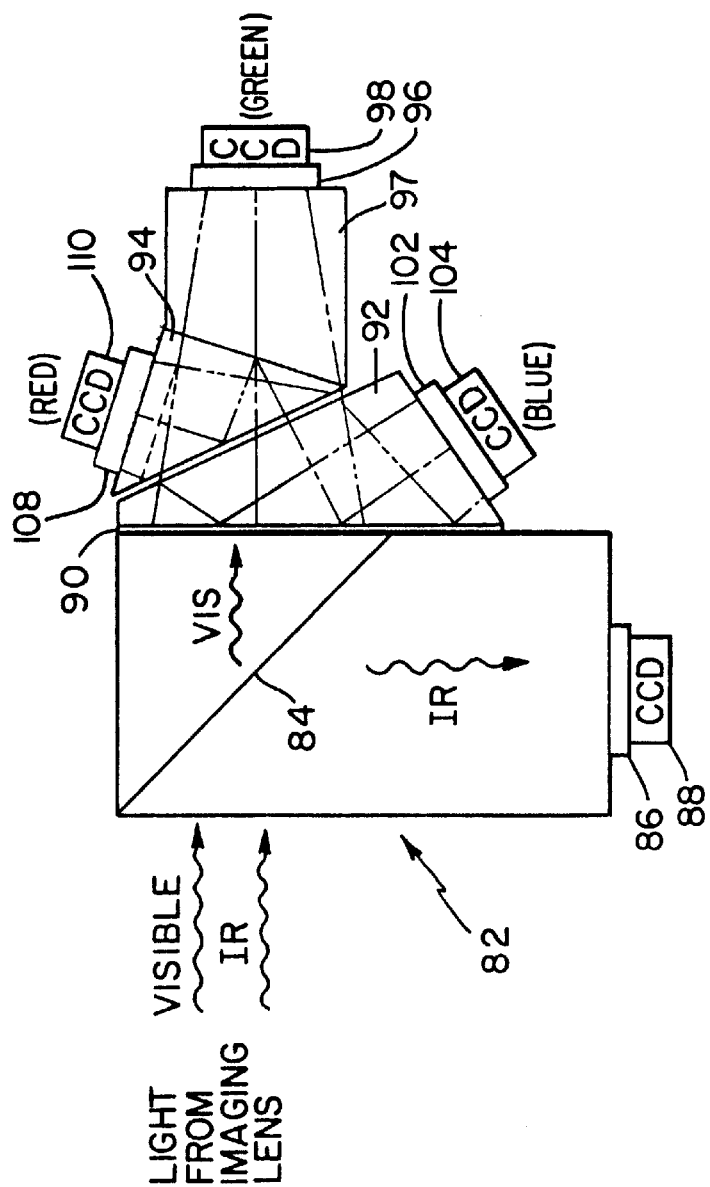
FIG. 7 illustrates a prism system for separating infrared light and the red, green and blue light signals of a visible light spectrum.

Referring now specifically to FIG. 7 of the accompanying drawings, there is illustrated another method of producing separate red, green and blue signals for subsequent processing.

A beam splitter prism 82 employs a dichroic filter 84 to separate visible light energy from infrared light energy. As in the embodiment of FIG. 1 the infrared light energy is reflected from the filter 84 through a visible light blocking filter 86 to a CCD 88 associated with a monochrome camera sensitive to infrared light energy and thence to processing circuits.

The visible light proceeds along the optical path through an IR blocking filter 90 to a prism set 92, 94, 97 that splits the visible light into red, green and blue light energies. The green light energy proceeds directly along the optical axis and through a trim filter 96 to a CCD 98. Blue light energy is deflected from prism 94, back through prism 92, thru through a trim filter 102 to a CCD 104. Red light energy is deflected from the rear and then front surface of prism 94, through a trim filter 108 to a CCD 110.

The CCDs 88, 98, 104 and 110 are monochromatic and may be processed as discussed relative to the embodiment of FIG. 4.

Reference is now made to the feature of the invention that provides color correction and increases the gain of the apparatus to infrared light energy emitted from the ureter.

From the standpoint of spectral sensitivity, all commercially available endoscopic cameras use either single or three chip silicon photodiode CCDs. The typical current responsivity of silicon CCDs ranges from 300 nm to 1,150, peaking at approximately 900 nm. The endoscopic camera uses a single chip silicon CCD, and therefore is confined to the limitations of the silicon CCDs, i.e., in the present system wavelengths from 300 nm to 1,150 nm.

The imaging system of the present invention employs a different light filtering scheme. This significant modification is important when attempting to identify infrared transilluminated structures and allow true fidelity color imaging of the surgical field. The camera detects visible light in the same range as other commercially available single chip CCD endoscopic cameras. As a result of removal of the IR filter from the camera however, the camera detects infrared (see FIG. 8) as well as visible light. The IR filter is replaced with a sapphire window that readily passes IR flight energy as well as visible light. Thus, the camera can efficiently detect the infrared transilluminated ureters when used with the endoscope light sensor whereas typical endoscopic cameras cannot (FIG. 8). The only difference between the camera of the present invention and the commercially available camera employed herein is replacement of the IR blocking and color compensating filter with a sapphire filter that passes light in the range of 300–2700 nm.

Referring to FIG. 9 a light cable houses a filter 114 that blocks infrared light from an endoscopic light source and adds a cyan color to the light illuminating the surgical field. To the naked and unaided eye, the light exiting the light cable appears cyan in color. However, this cyan filtered light that illuminates the surgical field corrects or compensates for reflected light from organs and instruments during an endoscopic procedure that is captured by the camera. As previously indicated, the net effect is an improvement in the color fidelity of the imaged field, produced by the camera in accordance with the invention.

Figure 10:
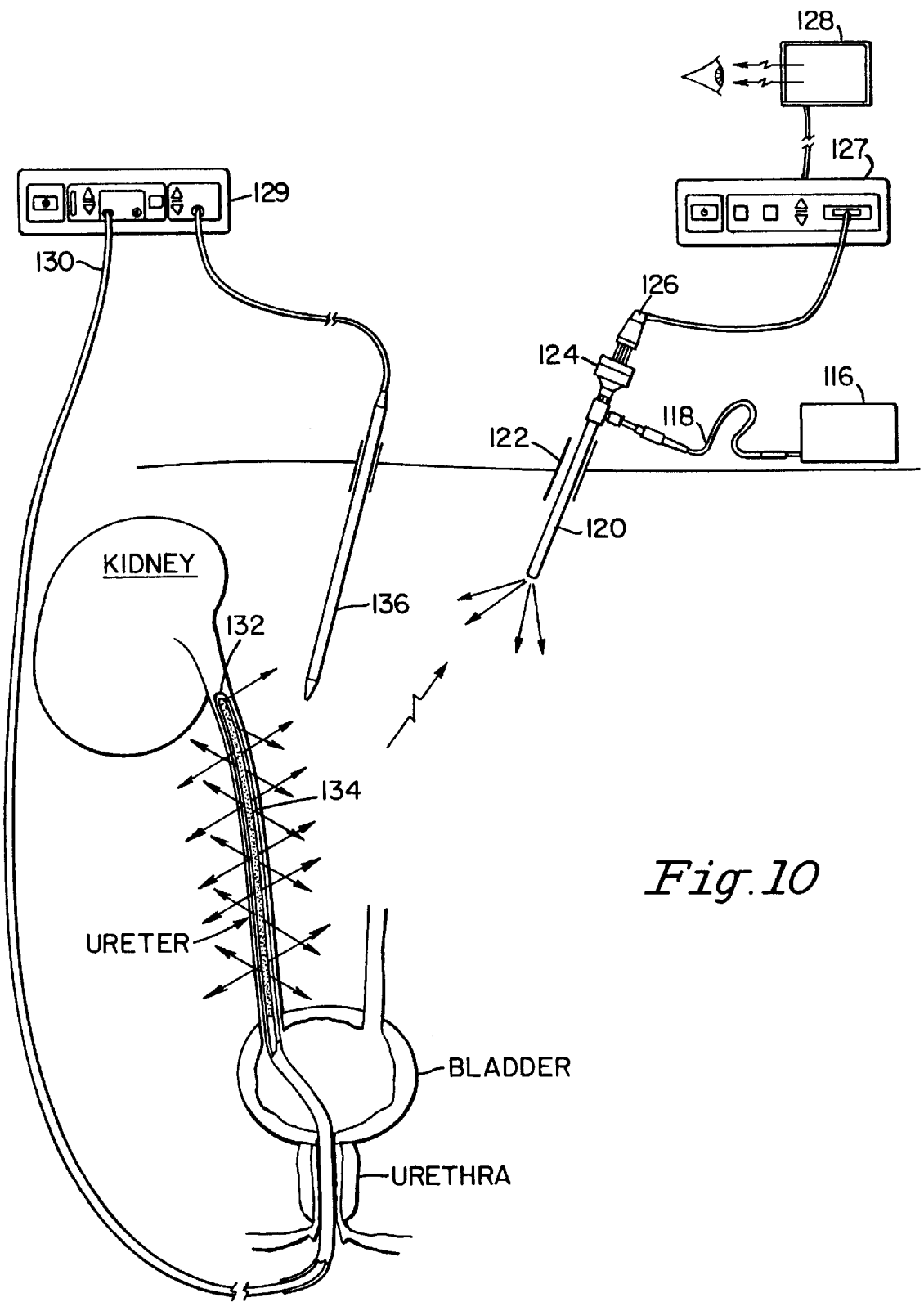
FIG. 10 illustrates a system employing the endoscope of FIG. 9.

Referring specifically to FIG. 10 of the accompanying drawings, a laparoscopic light source 116 supplies light energy via a light cable 118 to an endoscope 120. The cable includes, for instance, a CM500 filter from Hoya as illustrated in FIG. 9 and thus infrared light energy does not enter the endoscope. The endoscope 120 enters the body on which a procedure is being performed via a trocar 122 and illuminates the region of the procedure. Light form this region proceeds back through the endoscope, an optical coupler 124 to a laparoscopic camera 126 sensitive to both visible and infrared light energy in the range of light energy as depicted in FIG. 8. Signals produced by the camera 126 are supplied via a camera control unit 127 to a monitor 128 for viewing. The light path from the camera 126 to the unit 127 may includes any one of the configurations of FIGS. 1–7.

Infrared light energy is supplied by an infrared source and detector 129 to a light guide 130 that is located in a catheter 132 inserted into the ureter 134. The region of the light guide located in the ureter is conditioned to emit infrared light energy into the body cavity subject to the procedure. This light is detected by both the laparoscopic camera 126 and a probe 136 coupled to the source and detector 129. The surgeon or other investigator can now use the probe or the camera or both concurrently to locate the ureter, the camera to see the ureter and the probe to physically located it. Also the probe can be seen on the monitor and thus provides further help in locating the ureter.

The invention is not limited to use of a specific filter. The CM 500 is used with a Xenon or metal halide source while different filters may be employed with other light sources. In summary, the system of the present invention is a modular system that is adaptable.

1. The camera head has a sapphire cover over the CCD that allows all light in the range of 300 nm to 2,700 nm to reach the CCD. Thus, the camera is sensitive to light in the visible and infrared spectrum (as limited by the silicon CCD, i.e. 300 nm to 1,150 nm).
2. The light cable provides an infrared free abdominal-pelvic cavity during laparoscopy.
3. The light cable also adds cyan color to the light illuminating the surgical field to improve the color fidelity of the imaged surgical field using the camera of the present system.

Once given the above disclosure, many other features, modifications and improvements will become apparent to the skilled artisan. Such features, modifications and improvements are, therefore, considered to be a part of this invention, the scope of which is to be determined by the following claims.

What is claimed is:

1. A method of protecting body members from damage during surgery or other invasive body procedures from accidental trauma by producing images of the body members in the surgical site in a first spectrum and producing images in the surgical field of the body members to be protected that are not physically in the surgical field and are hidden therefrom in a second spectrum and processing the images of one of said spectra differently from the images of the other of said spectra comprising the steps of illuminating the surgical site to produce visible images in a first spectrum, causing images in a spectrum not visible to the human eye to be emitted by the body member to be protected and to appear in the surgical site, producing images in both spectra along a common optical path, separating the images of the two spectra, producing signals each developed from the images of a different spectrum, processing the signals produced by the signals of at least one of the spectra to enhance its image, and selectively displaying the images representative of the two spectra.

2. The method of claim 1 including the step of displaying the images on a video monitor.

3. The method of claim 1 wherein
separation of the light signals is accomplished by passing the images of both spectra in the optical path through a prism having an infrared reflecting filter lying at an angle to the common optical path.

4. The method of claim 1 further comprising the step of altering the color of images in said first spectrum.

5. The method of claim 1 wherein
the signals of the first spectrum are signals conveying information of color emitting sources, and
the signals of the second spectrum are signals conveying information of an infrared emitting source and further comprising the step of
displaying the color and infrared images selectively on a color monitor.

6. The method of claim 5 further comprising
sensing said signals of said first spectrum by a color video camera, and
sensing said signals of said second spectrum by a monochrome video camera sensitive to infrared light energy.

7. The method of claim 1 wherein
separation of the light signals is accomplished by inserting into said optical path selectively a first filter capable of passing light signals of the second spectrum only and at least a second filter that passes only light signals of the first spectrum.

8. The method of claim 7 wherein the light signals of the first spectrum are separated by having sequentially arranged red, green and blue filters rotating wheel located in the path of the separated color signals.

9. The method of claim 7 wherein the light signals of at least the first spectrum are separated by prisms into red, green and blue light signals.

10. The method of claim 7 further comprising
sensing the signals of both spectra by a monochrome video camera sensitive to light energy in both spectra to produce monochrome signals representing infrared and red, green and blue signals and
selectively reproducing colors of the original spectra.

11. The method of claim 10 wherein
the filter for the signals of the first spectrum passes selectively colors of the first spectrum, and
processing the monochrome signals representing the red, green and blue signals to reproduce the original color.

12. The method of claim 11 wherein
signals of the first spectrum representing red, green and blue may be passed selectively.

13. The method of claim 1 further comprising the step of adding color to the images of said second spectrum.

14. The method of claim 7 further comprising
sensing which filter is in the optical path, and
changing the processing of the signals as a function of the filter in the optical path.

15. The method of claim 14 further comprising
recombining the signals produced by the separate processing of the signals of the two spectra and displaying the images produced on a color monitor.

16. The method of claim 13 further comprising
the step of selectively displaying the colors of the signals representing the images of the first spectrum.

17. The method of claim 1 further comprising
passing signals of the first spectrum through a liquid crystal filter and
altering characteristics of the liquid crystal filter to pass light of different color spectra.

18. A system for preventing damage to body members adjacent to but not visible in or located at a site of a body invasive procedure due to intervening tissue, said system comprising
an imaging system with independent visual and infrared display,
means for transmitting an image of said body members into the site of the procedure by transmitting infrared light energy through the intervening tissue, and
a prism having a filter lying at an angle to a light path containing visible and infrared light energy,
said filter transmitting visible light energy and reflecting infrared light energy,
a first video camera sensitive to and positioned to receive said visible light energy and rendered insensitive to infrared light energy,
a second video camera sensitive to and positioned to receive infrared light energy substantially only,
each said video camera producing signals indicative of the light energy directed thereto,
different means for processing each of said signals, and
means capable of visually displaying said signals together after processing.

19. The system of claim 18 comprising
a video monitor, and
means for displaying the signals on said video monitor.

20. The system of claim 18 wherein
said video monitor is a color display monitor.

21. The system of claim 18 wherein
said first video camera is a color camera and said second video camera is a monochrome camera,
said means for processing signals from said second camera having means for adding signals indicative of color to said signals from said second video camera.

22. The system of claim 18 wherein said means for separating said infrared and visible light energy comprises,
a filter disposed in said light path and including separate visible light energy and infrared light energy segments,
means for causing one or the other of the segments to conduct light energy along the light path, and
means for processing the light energy passed by each said segment as a function of the filter in the light path.

23. The system of claim 22 wherein said means for rendering visible the combined signal comprises
a color video monitor.

24. The system of claim 22 wherein said filter comprises
red, green and blue and infrared light transmitting segments,
means for selectively inserting into the light path said red, green, blue and infrared light transmitting segments,
means for displaying at least one of the light segments to reproduce visual image signals.

25. The system of claim 22 including
a lookup table for determining the amount of each color to be added to reproduce color images, and
gating means for interrogating the look-up table.

26. The system of claim 22 wherein
said filter is a slide having filters passing visible and infrared light energy disposed on separate segments of said filter.

27. The system of claim 22 wherein
said filter includes a liquid crystal filters and
means for selectively controlling the light spectrum passed by said liquid crystal filter.

28. The system of claim 27 wherein
said filter includes a liquid crystal filter for selectively passing at least each color,
said filters disposed in series in the light path.

29. The system of claim 28 wherein
said filter also includes an IR filter in series in said light path.

30. The system of claim 28 further comprising
prism means for separating red, green and blue light energy into separate paths.

31. A system for preventing damage to body members according to claim 28 further comprising
a source of light for illuminating the site of the body invasive procedure,
a filter in the path of the light to the site of the procedure,
said filter blocking infrared light energy and providing color compensation.

32. A system for preventing damage to body members according to claim 22 further comprising
a source of light for illuminating the site of the body invasive procedure,
a filter in the path of the light to the site of the procedure,
said filter blocking infrared light energy and providing color compensation, and
means for directing light in said site to said imaging system.

33. A system for preventing damage to body members according to claim 31 wherein
said filter is a Hoya CM500.

34. A system for preventing damage to body members according to claim 31 further comprising
an endoscope,
said filter disposed between said light source and said endoscopes.

35. A system for protecting body members from damage during surgery or other invasive body procedures from accidental trauma by producing images of the body members in the surgical site in a first spectrum and producing images in the surgical field of the body members to be protected that are not physically in the surgical field and are hidden therefrom in a second spectrum and processing the images of one of said spectra differently from the images of the other said spectra comprising,
means for illuminating a surgical site,
said means including a source of broad spectrum light energy,
means for introducing the light into the surgical site,
a filter located between said source and said means for introducing,
means for viewing the site,
said filter removing infrared light energy from the light introduced into the surgical site and providing color compensation to provide color corrected light to the means for viewing.

36. A system according to claim 18 further comprising
means for separating the information conveyed by the infrared light energy and the information conveyed by the visible light energy for separate processing.

* * * * *

UNITED STATES PATENT AND TRADEMARK OFFICE
CERTIFICATE OF CORRECTION

PATENT NO. : 5,910,816
DATED : June 8, 1999
INVENTOR(S) : Mark G. Fontenot et al.

It is certified that error appears in the above-identified patent and that said Letters Patent is hereby corrected as shown below:

On title page, item [54] and column 1, lines 1-3, should read as follows:

--IMAGING SYSTEM WITH INDEPENDENT PROCESSING OF VISIBLE AND INFRARED LIGHT ENERGY--

Signed and Sealed this

Second Day of November, 1999

Attest:

Attesting Officer

Q. TODD DICKINSON

Acting Commissioner of Patents and Trademarks